United States Patent [19]

Miyairi et al.

[11] 4,160,698
[45] Jul. 10, 1979

[54] ENZYME IMMOBILIZATION WITH AZIDO COMPOUNDS

[75] Inventors: Sachio Miyairi, Chigasaki; Hideaki Tanaka, Hiratsuka; Akira Yabe, Fujisawa; Koichi Honda, Tokyo, all of Japan

[73] Assignee: Agency of Industrial Science & Technology, Ministry of International Trade & Industry, Tokyo, Japan

[21] Appl. No.: 831,649

[22] Filed: Sep. 8, 1977

[30] Foreign Application Priority Data

Sep. 9, 1976 [JP] Japan ............................ 51/108154

[51] Int. Cl.² ............................................. C07G 7/02
[52] U.S. Cl. .................................... 435/173; 435/180
[58] Field of Search .................... 426/63, 68, DIG. 11

[56] References Cited

U.S. PATENT DOCUMENTS

| 3,843,447 | 10/1974 | Burkoth | 195/68 |
|---|---|---|---|
| 3,959,078 | 5/1976 | Guire | 195/63 |
| 3,985,617 | 10/1976 | Yagari et al. | 195/63 |
| 4,004,979 | 1/1977 | Arrameas et al. | 195/68 |

*Primary Examiner*—David M. Naff
*Attorney, Agent, or Firm*—Oblon, Fisher, Spivak, McClelland & Maier

[57] ABSTRACT

A given enzyme is immobilized by a method comprising the steps of mixing the enzyme with an azido compound and a high molecular compound as a carrier, forming the resultant mixture in a desired shape, drying the formed mixture and exposing the formed and dried mixture to light for thereby causing the enzyme to be bound to the azido group of the azido compound and to be bound to the high molecular compound.

11 Claims, No Drawings

ENZYME IMMOBILIZATION WITH AZIDO COMPOUNDS

BACKGROUND OF THE INVENTION

This invention relates to a method for the immobilization of an enzyme by use of light.

At present, enzymes are extensively utilized for the manufacture of pharmaceutical products and food products, for the decomposition, synthesis and determination of various substances and for other purposes.

In enzymatic reactions carried out for these purposes, enzymes immobilized as by being entrapped within microorganic cells, deposited on carriers, combined with each other or similarly treated exhibit enhanced activities for longer lengths of time as compared with enzymes which are used in unimmobilized forms and are, furthermore easier to handle. Thus, there have heretofore been proposed numerous methods for immobilizing enzymes by use of specific reagents or cross-linking agents. Examples of U.S. patents which disclose these methods are U.S. Pat. No. 3,843,442, U.S. Pat. No. 3,950,222, U.S. Pat. No. 3,985,617, U.S. Pat. No. 3,985,618 and U.S. Pat. No. 3,933,587.

Besides, a method whereby immobilization of an enzyme is effected by use of light has been disclosed in "Chemical Abstracts," Vol. 85, page 244, 106024f. This method immobilizes a given enzyme by using an oligomer as a carrier and subjecting the enzyme to a cross-linking thermal reaction and a cross-linking photoreaction in the presence of an initiator for thereby causing the enzyme to be entrapped in the lattice of the resultant gelled polymer.

An object of the present invention is to provide a method for easily immobilizing a given enzyme with substantially no inactivation of the enzyme by use of light.

Another object of this invention is to provide a method for producing an immobilized enzyme preparation possessing desired mechanical properties.

SUMMARY OF THE INVENTION

To accomplish the objects described above in accordance with the present invention, there is provided a method for the immobilization of an enzyme which comprises mixing a given enzyme with an azido compound containing at least one aromatic group and a water-soluble high molecular compound, forming the mixture in a desired shape and exposing the formed mixture to light for thereby causing the enzyme to be bound to the azido group in the azido compound.

Since the method of this invention causes the enzyme to be bound to the azido group, the enzyme will not be dissolved out of the enzyme preparation obtained while the enzyme preparation is in use. Since none of the treatments involved in the immobilization by the method of the present invention is performed under any harsh condition, the enzyme undergoes absolutely no inactivation throughout the entire course of immobilization. Further, the mechanical properties of the immobilized enzyme preparation obtained by this method can freely be changed by suitably selecting the amount and kind of the high molecular compound to be incorporated during the preparation of the mixture. Thus, an enzyme preparation possessed of flexibility or an enzyme preparation excelling in permeability to liquids, for example, can be obtained by making a suitable selection.

DESCRIPTION OF PREFERRED EMBODIMENT

It has heretofore been known in the art to immobilize a given enzyme by combining the enzyme with a carrier or with another enzyme in some way or other through the medium of a cross-linking reagent or by entrapping the enzyme with a carrier.

The conventional method which accomplishes the desired immobilization of an enzyme by use of a cross-linking reagent, however, has not proved completely satisfactory because of inactivation of the enzyme during the treatment for immobilization, insufficient strength of immobilization and high production cost.

The inventors continued devoted studies with a view to overcoming the various disadvantages suffered by the conventional immobilized enzymes. They have consequently made a discovery that a specific azido compound is caused through the agency of light to react as with the $\gtrdot$CH group, the $\gtrdot$CH$_2$ group, etc. of the carrier or the amino acid which is one component of the enzyme proteins to give rise to a cross-linkage and that this formation of the cross-linkage is effective in the immobilization of an enzyme. The present invention has been accomplished on the basis of this discovery.

To be specific, the method according to the present invention effects the manufacture of an immobilized enzyme preparation by mixing and dissolving the given enzyme with an azido compound and a high molecular compound as a carrier, then through evaporation forming the resultant mixed solution into a film or pellets and thereafter exposing the formed mixture to light for thereby causing the enzyme to be bound to the azido group of the azido compound.

The azido compound to be used in the present invention is an azido compound which has at least one aromatic group of the generic formula:

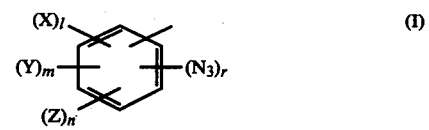

wherein, X, Y and Z each represent a member selected from the group consisting of halogen atoms, alkyl, alkoxyl and hydroxyl groups and salts thereof, sulfonic acid group and salts thereof, carboxyl group and salts thereof, l, m and n each represent an integer having a value of from 0 to 4 and r represents an integer having a value of from 1 to 5.

In the case of azido compounds containing two such aromatic groups, there are those in which the two aromatic groups are directly connected to each other and those in which they are connected by means such as of S, O, CO, NH, CH=CH—, —CH$_2$, etc.

The azido compounds satisfying the foregoing requirement are broadly divided into two types, i.e. aromatic azido compounds and water soluble high molecular compounds containing an azido group. When a compound of the former type is used, the reaction proceeds so that the enzyme units (E) are immobilized to the high molecular compound units (carrier) (C) via the compound units (B) in a configuration wherein either end of each compound unit (B) is connected to an enzyme unit (E) or a carrier unit (C) such as diagrammatically illustrated below, for example.

—(C)—(B)—(E)—(B)—(E)—(B)—(C)—(B)—(E)—

When there is used a compound of the latter type containing an azido group, since the compound contains a high molecular compound from the beginning, it is not always required to add a high molecular compound as a carrier during the preparation of a mixed solution. In this case, the reaction proceeds so that the enzyme units (E) are bound to the azido groups of the compound units (A). One example of the reaction is as illustrated below.

In the former reaction, there is a possibility that the azido compound units will bind the high molecular compound (carrier) units mutually in the manner of cross-linkage to give rise to a reticular configuration. In the latter reaction, it is not unlikely that high molecular compound units each containing an azido group will mutually react with one another and will consequently be bound to one another, thus giving rise to a reticular configuration. It is, therefore, quite possible that the enzyme units will be immovably enclosed in such a reticular configuration even if they are not allowed to react directly with azido group units.

Of the azido compounds usable for this invention, the aromatic diazido compounds or bis-azido compounds are represented by the following three generic formulas:

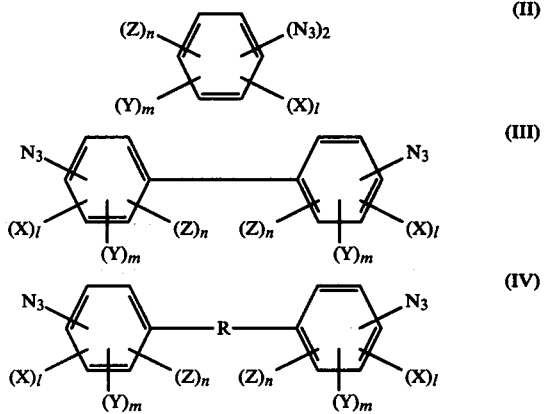

wherein, l, m and n each represent an integer having the value of from 0 to 4, X, Y and Z each represent one member selected from the class consisting of halogen atoms, alkyl, alkoxyl and hydroxyl groups and salts thereof, sulfonic acid group and salts thereof and carboxyl group and salts thereof and R represents
$-(CH_2)_p-$, $-(CH=CH)_q-$
(where, p and q each represent an integer having the value of from 1 to 3), an oxygen atom, a sulfur atom, $SO_2$ group or NH group.

In the case of 4,4'-diazido-stilbene-2,2'-disulfonic acid, as an example of the aromatic diazido compound, the formation of the cross-linkage by the photoreaction proceeds as shown below.

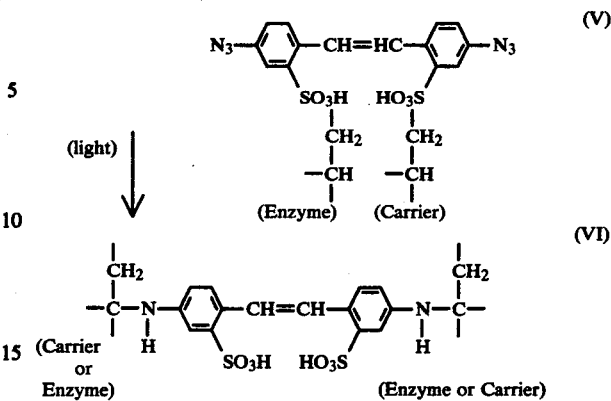

The soluble high molecular compounds containing an azido group are represented by the following two generic formulas:

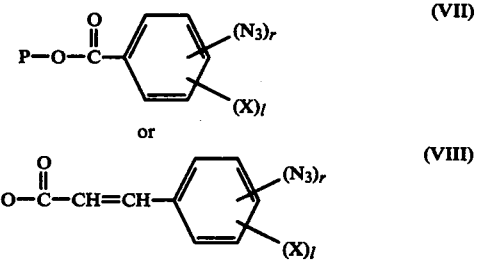

wherein, P represents a water soluble high molecular compound moiety selected from the group consisting of polyvinyl alcohols, cellulose, novolak resins, agar and scleroproteins (gelatin, collagen, fibroin and keratin), l represents an integer having the value of from 0 to 4 and r represents an integer having the value of from 1 to 5.

The water soluble high molecular compounds containing an azido group can easily be synthesized by the reaction of the water soluble high molecular compounds and azido compounds which reaction involves the esterification between the hydroxyl group constituting part of the structures of the high molecular compounds and the carboxyl group present in the azido compounds.

In the case of polyvinyl alcohol-p-azido-benzoic acid ester as one example of the high molecular compounds containing an azido group, the formation of the cross-linkage by the photoreaction is estimated to proceed as shown below.

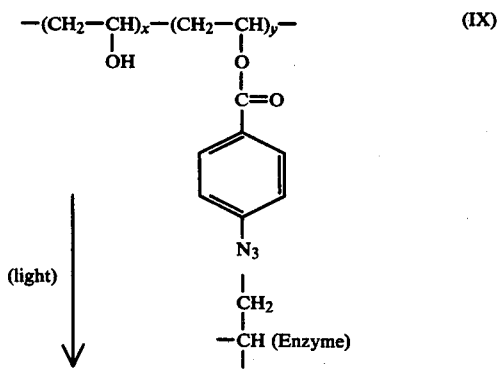

-continued

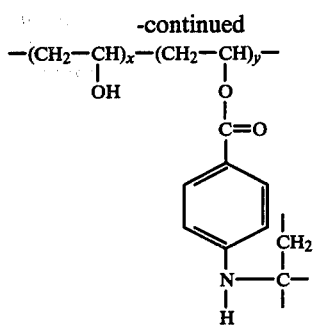

wherein x and y are positive integers having respective values such as to satisfy $100 < x+y < 2,000$ and $0.01 < \frac{y}{x+y} < 0.1$.

The enzymes which can be immobilized by the azido compounds described above include those of the classes of oxidoreductases, transferases, hydrolases, lyases, isomerases, ligases, etc. To be more specific, examples of oxidoreductases include glutamate dehydrogenase, lactate dehydrogenase, glyceraldehyde-phosphate dehydrogenase, glucose-6-phosphate dehydrogenase, malate dehydrogenase, isocitrate dehydrogenase, alcohol dehydrogenase, glucose oxidase, D-amino-acid oxidase, L-amino-acid oxidase, xanthine oxidase, protocatechuate 3,4-oxygenase, lipoxygenase, tyrosinase and pyridinenucleotide transhydrogenase.

Examples of transferases include pyruvate kinases, creatine kinase and t-RNA nucleotidyltransferase.

Examples of hydrolases include α-glucosidase, β-glucosidase, α-galactosidase, β-galactosidase, invertase, glucoamylase, lysozyme, hyaluronidase, urease, acid phosphatase, alkaline phosphatase, asparaginase, ficin, apyrase, prolidase, trypsin, α-chymotrypsin, papain, pepsin, pronase, subtilisin, carboxypeptidase A, carboxypeptidase B, lipase, ATPase, RNase, acetylcholinesterase and penicillinase.

Examples of lyases include aldolase, citrate synthase, ATP deaminase and AMP deaminase.

Examples of isomerases include glucose isomerase, glucose-phosphate isomerase and alanine racemase.

An example of ligase is succinyl-CoA synthetase.

As the carrier, any high molecular compound can be used insofar as it possesses a $\geqslant$CH group or a $\geqslant CH_2$ group. Examples of high molecular compounds usable for this purpose include water-soluble natural high molecular compounds such as cellulose, agar, scleroproteins (gelatin, collagen, fibroin and keratin) and water-soluble synthetic high molecular compounds such as polyvinyl alcohols, polyvinyl pyrrolidone and polyacrylamides.

To obtain the immobilized enzyme by the method of this invention, the proportions in which the aromatic diazido compound or bis-azido compound, the enzyme and the carrier are admixed are such that, for the fixed proportion of about 5% by weight of the compound, the proportion of the enzyme falls in the range of from about 1 to about 20% by weight and that of the carrier falls in the range of from about 94 to about 75% by weight.

When a high molecular compound containing an azido group is used as the azido compound in the preparation of the mixture, since the high molecular compound functions not merely as a cross-linking agent but also as a carrier, there is no particular need for using a high molecular compound specifically designed as a carrier. In this case, the immobilized enzyme can be advantageously obtained by using about 99 to about 80% by weight of the high molecular compound containing an azido group and about 1 to about 20% by weight of a given enzyme. The mechanical properties of the immobilized enzyme preparation to be obtained by the method of this invention rely upon the properties of the high molecular compound in any event. It is, therefore, possible to modify the mechanical properties of the immobilized enzyme preparation to be obtained finally by suitably decreasing the proportion of the high molecular compound to be added in the preparation of the mixture and adding the high molecular compound functioning solely as a carrier in a proportion to make up for the decrease. In this case, the proportion of the high molecular compound to be added as the carrier has an upper limit of about 70% by weight.

Depending on the purpose for which the immobilized enzyme is used, the mixing proportions of the azido compound, the enzyme and the high molecular compound can be freely changed within their respective ranges mentioned above. Particularly by changing the kind and the proportion of addition of the high molecular compound, there can easily be obtained immobilized enzyme preparations whose mechanical properties such as permeability to liquids and plasticity are varied as desired.

When collagen is selected as the high molecular compound and is added in a proportion of about 50%, for example, there is obtained a supple immobilized enzyme membrane having high plasticity. When keratin is added as the high molecular compound in a proportion of about 50%, there is obtained a rigid immobilized enzyme membrane having low plasticity. By pulverization, this membrane is converted into an immobilized enzyme in the form of pellets.

When glycerin is added in a proportion of 20 to 30%, for example, besides the high molecular compound, there is obtained a highly plastic and porous immobilized enzyme membrane excelling in permeability.

The immobilized enzyme in the form of a film is obtained by dissolving the azido compound, the enzyme and the high molecular compound in water, casting the resultant mixed solution on a horizontal plate and evaporating water from the solution. The immobilized enzyme in the form of pellets is obtained by spray drying the mixed solution in a hot-air fluidizing zone maintained at a temperature not so high as to inactivate the enzyme.

The formed immobilized enzyme obtained as described above is then exposed to light. As the source of this light, there can be used a high-pressure mercury lamp, a carbon arc, a luminescent lamp, sunlight, or the like.

The duration of the exposure to the light depends upon various factors such as the kind and concentration of the azido compound, the shape of the formed immobilized enzyme, the intensity of the light used for the exposure, etc. The photoreaction caused in the formed mixture by the agency of light can be considered to be complete when the cumulative decrease in the azido group content of the formed mixture totals slightly over 50%. And the cumulative decrease can be easily traced by testing the formed mixture for infrared absorption at 2100 to 2300 cm$^{-1}$ at proper intervals.

For example, when the mixture formed in the shape of a film 0.05 to 0.2 mm in thickness is exposed to the light from a 500-watt high-pressure mercury lamp, a duration of from 10 to 60 minutes suffices for required exposure, the variation depending somewhat on the type and concentration of the azido compound in use. A duration of from 10 to 24 hours is required, however, where the exposure is performed by use of a 40-watt luminescent lamp.

As for the temperature of the formed mixture during its exposure to light, the only requirement is that this temperature should not be so high as to inactivate the enzyme contained in the mixture. Where the enzyme happens to be of a type readily inactivated by heat, the photoreaction can easily be caused at amply low temperatures such as +10° to −50° C., for example.

The immobilized enzyme preparation thus obtained as a consequence of the photoreaction can be used similarly to any ordinary enzyme. In the case of an immobilized enzyme preparation in the shape of a film, effective use thereof can be obtained by immersing the preparation in a given reaction solution and agitating the solution. Effective use of an immobilized enzyme preparation in the shape of pellets is obtained by packing a column with the pellets and passing a given reaction solution through the column. Since, in the case of the present invention, the immobilized enzyme preparation can be produced in the form of a film of any desired shape, an immobilized enzyme membrane having permeability may be formed in a shape conforming to the cross section of a reaction cell and placed in a reaction vessel to partition the interior of the reaction vessel into two halves. The reaction vessel thus partitioned is usable in an operation wherein a high molecular substrate is placed in one of the two halves of the vessel interior and a low molecular substrate produced by the enzymatic reaction involving the immobilized enzyme present in the partitioning membrane is obtained in the remaining half of the vessel interior. Of course, the immobilized enzyme preparation in the form of a film can be cut up into pellets and used in the form of pellets.

As is evident from the foregoing description, the immobilization of a given enzyme according to this invention relies on the binding of the azido group of the azido compound to the enzyme. Thus, the enzyme is retained so strongly by the azido group that it will not be dissolved out while the immobilized enzyme preparation is in use in the reaction. Further since this immobilization is wholly carried out effectively at temperatures below the inactivating temperature of the enzyme, substantially all the enzyme that is used in the preparation of the mixture can be immobilized. By changing the type and the amount of addition of the high molecular compound also incorporated in the preparation, the resultant immobilized enzyme preparation can be given desired mechanical properties. Moreover, the immobilized enzyme preparation can easily be formed into any desired shape.

Now, the present invention will be described specifically with reference to examples, which are solely illustrative of and not limitative of the present invention.

EXAMPLE 1

1 g of commercially available gelatin (having a molecular weight of 100,000) was, as a carrier, placed in 10 ml of water and heated at about 60° C. to dissolve in the water. After the temperature of the resultant solution was lowered to 30° C., the solution was mixed with 5 ml of an aqueous 20 mg/ml β-glucosidase solution and 5 ml of an aqueous 10 mg/ml 4,4'-diazidostilbene-2,2'-disulfonate solution and agitated to uniformity, with the temperature kept at 30° C. The resultant solution was cast to a uniform thickness on a titanium plate having a smooth surface and left to stand overnight at room temperature (about 20° C.) so as to be dried. Consequently, there was obtained a thin membrane about 145 mm in length, about 120 mm in width and about 0.06 mm in thickness and about 1.1 g in weight.

Then, this thin membrane was exposed to the light from a 40-W luminescent lamp at 20° C. for 12 hours, washed with water and again left to stand on the plate to dry in the air.

The immobilized enzyme preparation thus obtained in the form of a film was assayed for protein content and tested for enzyme activity. The results indicate that in the course of the manufacture of the immobilized enzyme membrane, losses of the carrier and the enzyme were negligibly small. The weight ratio of the enzyme to the entire membrane was found to be about 9%.

An enzyme reaction was carried out as described below by using the immobilized enzyme membrane as the catalyst, to determine the yield of the activity of the membrane. In this reaction, p-nitrophenyl-β-D-glucopyranoside was used as a substrate and the activity was determined by measuring the amount of p-nitrophenol liberated in the absorption at 410 nm.

In 10 ml of water containing 180 mg of p-nitrophenyl-β-D-glucopyranoside, 20 mg of the immobilized enzyme membrane (containing 1.8 mg of enzyme) was gently shaken for 60 minutes under the conditions of 25° C. of temperature and pH 5.7 to induce a reaction. As the result of this reaction, a yield of the activity of 52% was obtained. The reason why the yield of the activity became one half of that of the native enzyme is not that the immobilization brings about the inactivation of the enzyme, but presumably that the rate at which the substrate is diffused in the membrane is slow and that the concentration of the substrate is lower in the solid state phase membrane than in the aqueous phase.

Further, the membrane was washed with water, dried in air and put to use again. When the membrane was tested for enzyme activity, there was obtained a yield of the activity of 48%. These results indicate that the immobilized enzyme preparation manufactured by the present invention retains a high stable activity.

For the purpose of determining the amount of enzyme dissolved out during the reaction, the membrane was removed from the solution and the remaining solution was similarly tested for enzyme activity. The solution showed no discernible enzyme activity in either of the two tests. The results indicate that in the immobilized enzyme membrane manufactured by the present invention, the enzyme is strongly immobilized.

The "yield of the activity" as used herein means the relative activity per unit weight of the enzyme immobilized, with the activity per unit weight of the initially incorporated enzyme taken as 100.

EXAMPLE 2

A thin membrane prepared by following the procedure of Example 1 was exposed to the light from a 500-W high-pressure mercury lamp at 20° C. for 10 minutes, then washed with water and dried. The resultant immobilized enzyme membrane was tested for yield of the activity. The yield was found to be about 54%. The yield of the activity was about 49% when the duration of the exposure to the light was increased to 60 minutes. Absolutely no dissolution of the enzyme was observed in either of the tests.

EXAMPLE 3

The procedure of Example 1 was repeated, except α-glucosidase and β-galactosidase were used as enzymes, to afford immobilized enzyme preparations each in the form of a film.

The film incorporating immobilized α-glucosidase and the film incorporating immobilized β-galactosidase were subjected to enzyme reaction, using p-nitrophenyl-α-D-glucopyranoside and p-nitrophenyl-β-D-galatopyranoside respectively as substrates, for 60 minutes under the conditions of 25° C. of temperature and pH 5.7, to determine their enzyme activities. The yield of the activity was found to be 47% for the former film and 49% for the latter film. Absolutely no dissolution of enzyme was recognized in either of the films.

EXAMPLE 4

In 5 ml of water heated to about 60° C., 0.5 g of gelatin was dissolved. The resultant solution was cooled to 30° C. This aqueous solution was mixed with 5 ml of an aqueous solution containing 0.5 g of polyvinyl alcohol (having a molecular weight of 60000). From this point onward, the procedure of Example 1 was repeated: The mixed aqueous solution was mixed with the same aqueous solution of β-glucosidase and 4,4'-diazidostilbene-2,2'-disulfonate, followed by thorough agitation to uniformity. The resultant mixture was then formed into a membrane and exposed to the light to afford an immobilized enzyme membrane. By repeating the procedure but using β-galactosidase instead of β-glucosidase, another immobilized enzyme membrane was similarly obtained.

The membrane incorporating immobilized β-glucosidase and the membrane incorporating immobilized β-galactosidase were subjected to enzymatic reaction, using p-nitrophenyl-β-D-glucopyranoside and p-nitrophenyl-β-D-galactopyranoside respectively as substrates, for 60 minutes under the conditions of 25° C. of temperature and pH 5.7, to determine their enzyme activities. The yield of the activity was found to be 48% for the former membrane and 45% for the latter membrane. Absolutely no dissolution of enzyme was recognized in either of the tests.

EXAMPLE 5

The immobilized enzyme membranes prepared in Example 4 were retained at room temperature (about 20° C.) for 50 days. Thereafter, they were tested for enzyme activities similarly to Example 4. The yield of activity was found to be 45% for the membrane incorporating immobilized β-glucosidase and 41% for the membrane incorporating immobilized β-galactosidase. Absolutely no dissolution of enzyme was recognized in either of the tests.

EXAMPLE 6

A polyvinyl alcohol (having a molecular weight of 60000) had its hydroxyl group partially esterified with p-azido-benzoic acid to an extent of being not completely deprived of water solubility. Two 10-ml portions of an aqueous solution each containing 1 g of the partial esterification product were mixed with 5 ml of an aqueous solution containing 50 mg of β-glucosidase and 5 ml of an aqueous solution containing 50 mg of β-galactosidase respectively, followed by thorough agitation to uniformity. The resultant mixtures were formed into membranes as in Example 1. These membranes were exposed to light as in Example 1, washed with water and then tested for enzyme activity. The yield of the activity was found to be 43% for the former membrane and 40% for the latter membrane. Absolutely no dissolution of enzyme was recognized in either of the tests.

EXAMPLE 7

To 8 ml of an aqueous solution containing 1 g of the same polyvinyl alcohol-p-azido-benzoic acid ester as prepared in Example 6, there was added 4 ml of an aqueous solution which contained 0.5 g of gelatin dissolved at 60° C. and which was thereafter cooled to 30° C. The resultant mixed solution was mixed with 3 ml of an aqueous solution having dissolved therein 50 mg of α-glucosidase, followed by thorough agitation to uniformity. This procedure was repeated, except there was used 3 ml of an aqueous solution having dissolved therein 50 mg of β-galactosidase. These mixtures were formed each in the form of a membrane, exposed to a light and washed with water similarly to Example 1. The resultant immobilized enzyme membranes were tested for enzyme activity similarly to Example 2.

The yield of the activity was found to be 39% for the former membrane and 38% for the latter membrane. Absolutely no dissolution of enzyme was recognized in either of the tests.

EXAMPLE 8

A polyvinyl alcohol (having a molecular weight of 60000) had its hydroxyl group partially esterified with p-azido-cinnamic acid to an extent of being not completely deprived of water solubility. 10 ml of an aqueous solution containing 1 g of the partial esterification product was mixed with 5 ml of an aqueous solution containing 50 mg of β-galactosidase, followed by thorough agitation to uniformity. The resultant mixture was formed into a membrane as in Example 1. The membrane was exposed to the light from a 500-W high-pressure mercury lamp at 20° C. for 20 minutes, washed with water and then tested for enzyme activity. The yield of activity was found to be 39%. Absolutely no dissolution of enzyme was recognized in this test.

What is claimed is:

1. A method for the immobilization of an enzyme comprising the steps of:
    mixing about 1 to about 20% by weight enzyme with an aromatic group-containing azido compound and a water-soluble high molecular weight compound, wherein said aromatic group containing azido compound is represented by formulae selected from the group consisting of I, II and III

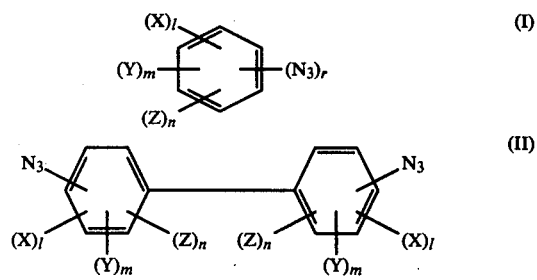

-continued

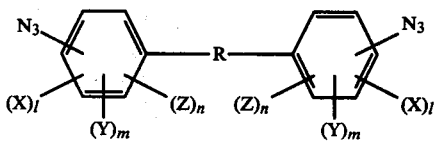
(III)

wherein X, Y and Z each represent one member selected from the group consisting of halogen atoms, alkyl, alkoxyl and hydroxyl groups and salts thereof, sulfonic acid group and salts thereof; l, m and n each represent an integer having the value of from 0 to 4 and, r represents an integer having the value of from 2 to 5; wherein R represents $-(CH_2)_p-$, $-(CH=CH)_q-$, wherein p and q represent an integer having the value of from 1 to 3, an oxygen atom, a sulfur atom, $SO_2$ group or NH group;

forming the resultant mixture into a desired shape; drying said shaped mixture; and exposing the dried mixture to light to cause the water soluble high molecular weight compound to be bound to one azido group of said azido compound and the enzyme to be bound to another azido group of said azido compound, whereby the enzyme becomes bound to said water soluble high molecular weight compound.

2. The method according to claim 1, wherein the azido compound contains a hydrogen atom in the aromatic group represented by said generic formula (I).

3. The method according to claim 1, wherein said azido compound is represented by the formula

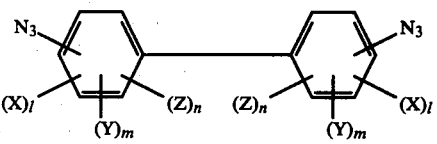
(II)

4. The method according to claim 1 wherein said azido compound is represented by the formula

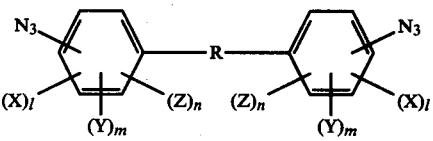
(III)

wherein R represents $-(CH_2)_p-$, $-(CH=CH)_q-$, wherein p and q represent an integer having the value of from 1 to 3, an oxygen atom, a sulfur atom $SO_2$ group or NH group.

5. The method according to claim 1, wherein the azido compound is 4,4'-diazido-stilbene-2,2'-disulfonate.

6. The method according to claim 1, wherein the water-soluble high molecular compound is at least one member selected from the group consisting of cellulose, agar and scleroprotein.

7. The method according to claim 1, wherein the exposure to the light is performed at temperatures in the range of from 30° C. to −50° C.

8. A method for the immobilization of an enzyme comprising the steps of:

mixing about 1 to about 20% by weight enzyme with a water soluble high molecular weight azido group-containing compound represented by the formula:

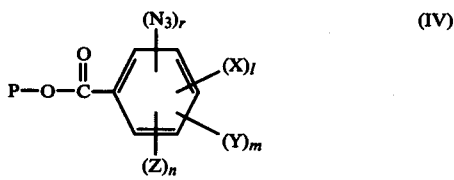
(IV)

wherein P represents a water-soluble high molecular compound which is selected from the group consisting of polyvinyl alcohol, polyvinyl pyrrolidone, polyacrylamide, cellulose, novolak resin, agar and scleroprotein; wherein X, Y and Z each represent one member selected from the group consisting of halogen atoms, alkyl, alkoxyl and hydroxyl groups and salts thereof, sulfonic acid group and salts thereof; l, m and n each represent an integer having the value of from 0 to 4 and, r represents an integer having the value of from 1 to 5;

forming the resulting mixture into a desired shape; drying said shaped mixture; and exposing the dried mixture to light thereby causing the enzyme to be bound to the azido group of said water soluble high molecular weight compound.

9. The method according to claim 8, wherein the azido compound is polyvinyl alcohol-p-azido-benzoic acid ester.

10. The method according to claim 8, wherein the water-soluble high molecular compound P of the formula is bound to the aromatic group of the formula through a vinylene group.

11. The method according to claim 10, wherein the azido compound is polyvinyl alcohol-p-azido-cinnamic acid ester.

* * * * *